United States Patent [19]

Decker et al.

[11] Patent Number: 4,764,309
[45] Date of Patent: Aug. 16, 1988

[54] PREPARATION OF CHLOROCARBOXYLIC ACID CHLORIDES

[75] Inventors: Martin Decker, Ludwigshafen; Franz Neumayr, Weisenheim, both of Fed. Rep. of Germany

[73] Assignee: BASF Aktiengesellschaft, Ludwigshafen, Fed. Rep. of Germany

[21] Appl. No.: 68,147

[22] Filed: Jun. 29, 1987

[30] Foreign Application Priority Data

Jul. 18, 1986 [DE] Fed. Rep. of Germany ....... 3624258

[51] Int. Cl.$^4$ ............................................. C07C 53/46
[52] U.S. Cl. ............................. 260/544 K; 260/544 Y
[58] Field of Search ...................... 260/544 K, 544 Y

[56] References Cited

U.S. PATENT DOCUMENTS

| | | | |
|---|---|---|---|
| 2,778,852 | 1/1957 | Adams et al. | 260/544 |
| 3,346,594 | 10/1967 | Merijan et al. | 260/544 Y |
| 3,544,626 | 12/1970 | Carr et al. | 260/544 K |
| 4,321,408 | 3/1982 | Maurer et al. | 260/544 K |

FOREIGN PATENT DOCUMENTS 1080261 12/1954 France.

OTHER PUBLICATIONS

Patai, Saul *The Chemistry of Acyl Halides*, (1972) Interscience, Publ. pp. 44–45.

*Primary Examiner*—Paul J. Killos
*Attorney, Agent, or Firm*—John H. Shurtleff

[57] ABSTRACT

Chlorocarboxylic acid chlorides of the formula

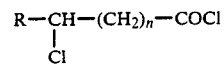

I where R is H or alkyl and n is an integer from 2 to 4, are prepared by reacting a lactone of the formula

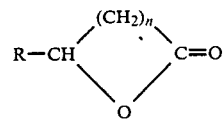

II with phosgene at elevated temperatures and in the presence of a quaternary ammonium salt.

12 Claims, No Drawings

PREPARATION OF CHLOROCARBOXYLIC ACID CHLORIDES

The present invention relates to a process for the preparation of chlorocarboxylic acid chloride by reacting a lactone with phosgene in the presence of a quaternary ammonium salt.

French Pat. No. 1,080,261 discloses that 4-chlorobutyryl chloride can be prepared by reacting 4-butyrolactone with phosgene at about 120° C., pyridine being used as a catalyst. Since it was not possible to reproduce the result stated in Example 2 of this patent, and over the past few years chlorocarboxylic acid chlorides have become increasingly important as intermediates for the preparation of drugs and crop protection agents, it was necessary to find a process which permits the preparation of chlorocarboxylic acid chlorides in good yields by an economical industrial procedure.

We have found that chlorocarboxylic acid chlorides of the formula

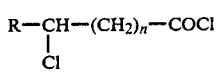

where R is H or alkyl and n is an integer from 2 to 4, can be particularly advantageously prepared by reacting a lactone of the formula

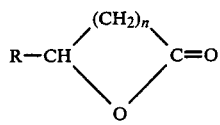

with phosgene at elevated temperatures if the reaction is carried out in the presence of a quaternary ammonium salt.

In the starting materials of the formula II, R is H or alkyl, for example alkyl of 1 to 3 carbon atoms. Examples of suitable lactones of the formula II are 4-butyrolactone, 5-methyl-4-butyrolactone, 5-valerolactone and 6-caprolactone.

The quaternary ammonium salts used are, for example, trimethylbenzylammonium chloride, N,N-dimethylpiperidinium chloride and dimethylmorpholinium chloride. They are used in amounts of from 0.5 to 5 mol %, based on the lactone. These compounds are not attacked by phosgene under the reaction conditions, and they therefore retain their activity for a very long time.

The novel process is carried out, for example, at from 60° to 200° C., preferably from 90° to 180° C. Advantageously, the following procedure is adopted: the lactone, in the presence or absence of an inert solvent, and the quaternary ammonium salt are initially taken, the mixture is heated to the reaction temperature and phosgene is then passed in. Phosgene is used in a stoichiometric amount or in greater amounts, for example up to 3 times the stoichiometric amount, the excess phosgene advantageously being condensed by cooling the exit gases to −40° C. or lower, preferably −70° C. or lower, and being recycled to the reaction vessel. Suitable inert solvents are solvents which do not react with the starting materials and the products under the reaction conditions, for example cumene and other high boiling hydrocarbons, as well as aromatic chlorine compounds, such as dichlorobenzene. In general, however, a solvent is not required. The process is advantageously carried out under atmospheric pressure or under pressures which differ only slightly from atmospheric pressure. It may be carried out batchwise or continuously.

In a particularly advantageous embodiment of the novel process, up to 100 mol %, based on the lactone, of hydrogen chloride or of a compound which forms hydrogen chloride with phosgene, for example water, is passed into the reaction vessel simultaneously with the phosgene. From 5 to 100, in particular from 20 to 40, mol %, based on the lactone, of hydrogen chloride or a substance which forms hydrogen chloride is preferably added. Surprisingly, it has been found that this addition greatly accelerates the conversion of the lactone to the chlorocarboxylic acid chloride. Even the addition of small amounts has a substantial effect. For economic reasons and because of the stripping effect on the phosgene dissolved in the reaction mixture, larger amounts of hydrogen chloride are not recommended.

The process of the invention gives the chlorocarboxylic acid chlorides smoothly and in high yield.

In the Examples, parts are by weight.

EXAMPLE 1

In a stirred reactor having a facility for feeding in hydrogen chloride and phosgene, 1032 parts of 4-butyrolactone and 54 parts of N,N-dimethylpiperidinium chloride are initially taken, and the internal temperature is brought to 130°–135° C. by means of a heating medium. At this temperature, 1200 parts of phosgene and 150 parts of hydrogen chloride are passed in over 10 hours. The phosgene is condensed out of the exit gas by cooling to −70° C. and is recycled to the reaction zone. When the addition is complete, the reaction mixture is kept at this temperature for a further 2 hours to complete the reaction. Thereafter, the 4-chlorobutyryl chloride is distilled off over a column under about 100 mbar. A further 1032 parts of 4-butyrolactone are added to the residue, which consists of monomeric and oligomeric 4-butyrolactone and the catalyst, and are reacted with phosgene and hydrogen chloride as described above. A total of 5160 parts of butyrolactone are used in this manner. Working up by distillation gives 8012 parts of 4-chlorobutyryl chloride, corresponding to a yield of 94.7 mol %.

EXAMPLE 2

430 parts of 4-butyrolactone and 47 parts of trimethylbenzylammonium chloride are initially taken in a 1 l stirred reactor which is equipped with a thermometer, inlet tubes for phosgene and hydrogen chloride and 2 low-temperature coolers set at −20° C. and −70° C. respectively. The mixture is heated to 130° C. 560 parts of phosgene and 120 parts of hydrogen chloride are passed in over 5.5 hours. Thereafter, nitrogen is passed in until the reaction mixture no longer contains any phosgene. Working up by distillation gives 620 g of 4-chlorobutyryl chloride and 30.5 g of butyrolactone. The distillation residue of 75 g, which consists of the catalyst and chlorobutyroyloxybutyryl chloride, can be reused for further batches. The yield of 4-chlorobutyryl chloride is 88 mol %, based on butyrolactone used.

EXAMPLE 3

A procedure similar to that described in Example 1 is used, and 100 parts of 4-valerolactone are treated with 80 parts of phosgene and 100 parts of gaseous hydrogen chloride in the presence of 4.5 parts of N,N-dimethylpiperidinium chloride at 140°-150° C. in the course of 10 hours. Working up and distillation similarly to Example 1 give 60.2 mol %, based on 4-valerolactone converted, of 4-chloropentanoyl chloride. The conversion is 54%. The yield can be further increased by reusing the oligomeric distillation residue.

EXAMPLE 4

A procedure similar to that described in Example 1 is used, and 100 parts of 5-valerolactone are reacted with 100 parts of phosgene in the presence of 4.5 parts of N,N-dimethylpiperidinium chloride at 170°-175° C. in the course of 2.5 hours. The conversion is 93%. Working up and distillation similarly to Example 1 give 76.3 mol %, based on converted 5-valerolactone, of 5-chloropentanoyl chloride. The yield of 5-chloropentanoyl chloride is further increased by reusing the oligomeric distillation residue in subsequent batches.

EXAMPLE 5

A procedure similar to that described in Example 1 is used, and 114 parts of 6-caprolactone are reacted with 100 parts of phosgene in the presence of 4.5 parts of N,N-dimethylpiperidinium chloride at 160°-170° C. in the course of 4.75 hours. The conversion is 78.9%. Working up and distillation similarly to Example 1 give 81.7 mol %, based on converted 6-caprolactone, of 6-chlorohexanoyl chloride. The yield of 6-chlorohexanoyl chloride is further increased by reusing the oligomeric distillation residue.

EXAMPLE 6

456 parts of 6-caprolactone and 9 parts of N,N-dimethylpiperidinium chloride are initially taken in the stirred reactor described in Example 1. 380 parts of phosgene and 70 parts of hydrogen chloride are passed in at 170°-175° C. in the course of 7 hours. The reaction mixture is then kept at this temperature for a further hour. Any phosgene and hydrogen chloride still present are blown out with nitrogen, and the reaction mixture is then worked up by distillation under reduced pressure. 424 parts of 6-chlorohexanoyl chloride and 86 parts of caprolactone are obtained. The conversion is 81% and the yield is 77.3%, based on lactone used.

EXAMPLE 7

A procedure similar to that described in Example 6 is used, and 200 parts of 5-valerolactone and 9 parts of dimethylpiperidinium chloride are heated to 175°-180° C. and reacted at this temperature with 230 parts of phosgene and 70 parts of hydrogen chloride. The reaction time is 3.75 hours. Dissolved phosgene and hydrogen chloride are then blown out with nitrogen, and the crude product is distilled under reduced pressure.

241 parts of 98.1% pure 5-chloropentanoyl chloride are obtained. The 52 parts of distillation residue contain the catalyst and unconverted 5-valerolactone, which are reused in subsequent batches. The yield is 76.2%, based on lactone used.

We claim:

1. In a process for the preparation of a chlorocarboxylic acid chloride of the formula

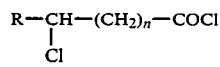

where R is H or alkyl and n is an integer from 2 to 4, by reacting a lactone of the formula

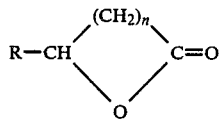

with phosgene at elevated temperatures, the improvement which comprises:
    carrying out the reaction in the presence of a quaternary ammonium salt.

2. A process as claimed in claim 1, wherein the lactone and the quaternary ammonium salt are initially taken into a reaction vessel, and the phosgene and up to 100 mol %, based on the lactone, of hydrogen chloride or of water which forms hydrogen chloride with phosgene is passed into the reaction vessel.

3. A process as claimed in claim 1, wherein the reaction is carried out at from 60° to 200° C.

4. A process as claimed in claim 1, wherein the reaction is carried out at from 90° to 180° C.

5. A process as claimed in claim 1, wherein from 5 to 100 mol %, based on the lactone, of hydrogen chloride or of water is used.

6. A process as claimed in claim 1, wherein the quaternary ammonium salt used is N,N-dimethylpiperidinium chloride.

7. A process as claimed in claim 1, wherein the quaternary ammonium salt is used in an amount of from 0.5 to 5 mol%, based on the lactone.

8. A process as claimed in claim 1, wherein the quaternary ammonium salt is used in an amount of from 0.5 to 5 mol%, based on the lactone.

9. A process as claimed in claim 8, wherein the lactone is 4-butyrolactone.

10. A process as claimed in claim 9, wherein the reaction is carried out at from 60° to 200° C.

11. A process as claimed in claim 9, wherein the quaternary ammonijm salt is N,N-dimethlpiperidinium chloride.

12. A process as claimed in claim 9, wherein from 20 to 40 mol%, based on the lactone of hydrogen chloride or water is used.

* * * * *